United States Patent [19]

Horner et al.

[11] 4,374,258
[45] Feb. 15, 1983

[54] CHROMAN-6-OL DERIVATIVES USEFUL FOR STABILIZING PLASTICS

[75] Inventors: Michael Horner, Neustadt; Gernot Teege, Ludwigshafen, both of Fed. Rep. of Germany

[73] Assignee: BASF Aktiengesellschaft, Fed. Rep. of Germany

[21] Appl. No.: 343,762

[22] Filed: Jan. 28, 1982

[30] Foreign Application Priority Data

Feb. 4, 1981 [DE] Fed. Rep. of Germany ....... 3103740

[51] Int. Cl.³ .......................................... C07D 311/72
[52] U.S. Cl. ................................ 549/407; 8/DIG. 9; 585/18
[58] Field of Search ................................ 549/408, 407

[56] References Cited

FOREIGN PATENT DOCUMENTS 1114319  4/1962  Fed. Rep. of Germany ...... 549/408
1139102  11/1962 Fed. Rep. of Germany ...... 549/408
2364141  6/1974  Fed. Rep. of Germany .
2364165  6/1974  Fed. Rep. of Germany .
3010505  10/1981 Fed. Rep. of Germany ...... 549/408

Primary Examiner—Nicky Chan
Attorney, Agent, or Firm—Keil & Witherspoon

[57] ABSTRACT

Novel chroman derivatives

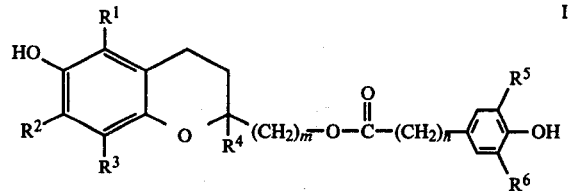

where $R^1$, $R^2$, $R^3$ and $R^4$ are each H or $C_1$-$C_4$-alkyl, $R^5$ is sec.—$C_3$-$C_8$—alkyl or tert.—$C_4$-$C_8$—alkyl, $R^6$ is H or $R^5$, m is 1, 2 or 3, and n is 0, 1, 2 or 3, a process for the preparation of these compounds, and their use as stabilizers for plastics.

1 Claim, No Drawings

CHROMAN-6-OL DERIVATIVES USEFUL FOR STABILIZING PLASTICS

The present invention relates to novel chroman derivatives of the general formula I

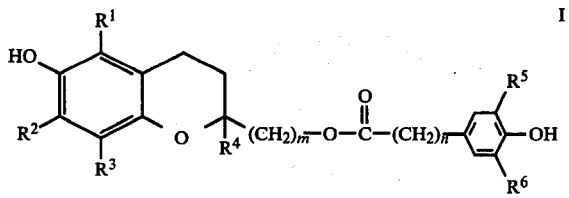

where $R^1$, $R^2$, $R^3$ and $R^4$ are each H or $C_1$–$C_4$-alkyl, $R^5$ is sec.-$C_3$–$C_8$-alkyl or tert.-$C_4$–$C_8$-alkyl, $R^6$ is H or $R^5$, m is 1, 2 or 3, and n is 0, 1, 2 or 3.

The invention further relates to the preparation of the compounds I, to their use as light stabilizers, heat stabilizers and oxidation stabilizers for plastics, and to the plastics stabilized with these compounds.

Chroman derivatives, especially α-tocopherol (vitamen E)

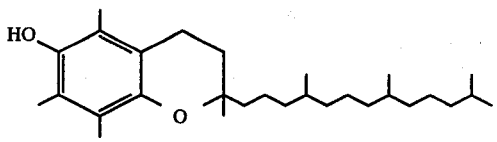

are well known as stabilizers for plastics and organic materials (cf. German Pat. Nos. 1,114,319 and 1,136,102).

Although α-tocopherol exhibits a good stabilizing action against the degradation of plastics during repeated processing by remelting, it is unsatisfactory in other respects. α-Tocopherol frequently causes discoloration and gives only unsatisfactory stabilization results in the oven aging test, which permits an estimate of the useful life of the plastic. From a processing point of view also, α-tocopherol, an oily substance prone to oxidation, presents problems. Furthermore, α-tocopherol is relatively expensive and is therefore only in exceptional cases suitable as an additive to mass-produced materials, such as plastics.

Although simpler chroman derivatives, such as those described in German Laid-Open Application DOS No. 2,364,141, are cheaper, they are also less effective overall.

It is true in general that particular stabilizers possess only a few useful stabilizing properties, while being deficient in other respects. For example, the commercial phenolic stablizers, eg. pentaerythrityl tetrakis-[3-(3,5-di-tert.-butyl-4-hydroxyphenyl)-propionate], provide good protection against the oxidative degradation of plastics, but not against degradation during processing and, in particular, repeated reprocessing.

For this reason, mixtures of various stabilizers have frequently been used, though this usually gives rise to technological difficulties.

It is an object of the present invention, as of the prior German Laid-Open Application DOS No. 3,010,505, to alleviate the above disadvantages and to provide industry with cheaper stabilizers having a broader spectrum of the desired stabilizing properties.

We have found that this object is achieved by the chroman derivatives I defined at the outset, which are exceptionally suitable for use as stabilizers for plastics.

Further, we have found various processes for the preparation of the chroman derivatives I, which are described in more detail below.

Amongst the compounds I, those where $R^1$, $R^2$, $R^3$ and $R^4$ are methyl are preferred, since chroman derivatives having this structure are particularly easy to prepare. Compounds I where $R^1$, $R^2$, $R^3$ and $R^4$ are each radicals other than methyl can be prepared in a similar manner, and their action as stabilizers is about the same as that of the tetramethylchroman derivatives.

An essential structure for achieving the stabilizing effect is the substituent $R^5$ in the ortho-position to the phenolic hydroxyl group. Although all secondary and tertiary alkyl groups according to the definition are basically suitable, compounds where $R^5$ is isopropyl or, especially, tert.-butyl are preferred for economic reasons. Furthermore, those compounds where $R^6$ is one of the radicals $R^5$ are preferred, since they possess a particularly powerful stabilizing effect in most cases. In contrast, the number of methyl groups m or n has no significant effect on the stabilizing action of the compounds I.

The chroman derivatives I are obtainable in a conventional manner by esterification of a chroman derivative II

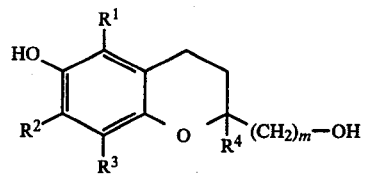

with a phenol derivative of the general formula III

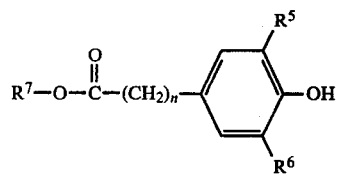

where $R^7$ is hydrogen or $C_1$–$C_4$-alkyl. The details of the numerous embodiments of the esterification ($R^7$=H) and trans-esterification ($R^7$=$C_1$–$C_4$-alkyl), in respect of the acidic or basic catalysts, the removal of the water of reaction or of the alcohols split off, the temperature and the reaction time, are well known, so that further explanation is unnecessary.

The purification of the compounds I, if necessary at all, can be carried out by recrystallization, for example from methanol/water.

The compounds II and their preparation have been disclosed in German Laid-Open Application DOS No. 3,010,504.

The majority of the phenol derivatives III are also known (cf. for example German Pat. No. 1,201,349) and can be prepared in general in a conventional manner, for example by the addition reaction of an acrylyl compound IV with a phenol V $$R^7-O-\overset{\overset{O}{\|}}{C}-CH=CH_2 + \underset{R^6}{\overset{R^5}{\underset{\|}{\bigcirc}}}-OH \longrightarrow III$$

IV    V

The novel derivatives I are outstandingly useful as heat stabilizers, light stabilizers and oxidation stabilizers for plastics. The stabilizing properties of the chroman derivatives I in sensitive plastics, such as polypropylene, polyisobutylene, styrene and acrylate/butadiene/styrene polymers, should be particularly singled out. Depending on the severity of the conditions to which these materials are exposed, the stabilizers are used in concentrations of from 0.005 to 1.0, as a rule from 0.01 to 0.5%, by weight, based on the amount of plastic.

The novel stabilizers may be used alone or mixed with other stabilizers, especially with synergistic agents. The latter are compounds which alone have little or no stabilizing effect but, when used conjointly with stabilizers markedly improve their effect. Examples of such synergistic agents are calcium stearate and distearyl thiodipropionate VI $$\overset{O}{\underset{\|}{S}}-(CH_2-CH_2CO\ stearyl)_2 \qquad VI$$

The synergistic agent is in general employed in an amount of from 50 to 500% by weight, based on the amount of stabilizer. However, the particular advantage of the novel stabilizers is that the presence of other stabilizers or synergistic agents is unnecessary in most cases.

The following criteria are particularly relevant in assessing the suitability and effectiveness of stabilizers:

1. Color

The stabilizer should not discolor the substrate. This requirement, which is of course particularly important for colorless plastics, is satisfactorily or excellently met by the novel stabilizers in the case of most plastics; as a rule, the novel compounds are superior to conventional stabilizers, including α-tocopherol. The quantitative determination of the color characteristics can be carried out by various methods, for example by the yellowness test—ASTMD 1925.

2. Processing stability

This refers to the degree to which the properties of thermoplastics remain constant when exposed to mechanical stresses and heat during molding processes, such as extrusion and injection-molding. In this respect, the novel stabilizers give particularly good results. A measure of the processing stability is the change in melt characteristics of the thermoplastic after repeated molding and remelting. The corresponding melt index test is described in DIN 53,735. Another important criterion of processing stability is constancy of color, which can be assessed by, for example, the yellowness test.

3. Long-term stability

The behavior of plastics when exposed to severe thermal and oxidative conditions is an indication of the period for which the quality of the plastic will remain constant when the material is used for a particular application; this means that the data determined by the corresponding test (DIN 53,383, page 1) permit an estimate of the useful life of the plastic article. The novel stabilizers offer advantages in long-term stability when used in conjunction with synergistic agents.

Further details concerning tests of the quality of the novel stabilizers are to be found in the experiments on the effects of the stabilizers.

EXAMPLES OF THE PREPARATION OF THE CHROMAN DERIVATIVES I

EXAMPLE 1

6-Hydroxy-2,5,7,8-tetramethyl-2-[3-oxa-4-oxo-7-(3,5-di-tert.-butyl-4-hydroxy)-phenyl]-hept-1-yl chroman A solution of 20 g (0.077 mole) of 3-(3,5-di-tert.-butyl-4-hydroxyphenyl)-propionic acid, 19.2 g (0.077 mole) of 6-hydroxy-2,5,7,8-tetramethyl-2-(2-hydroxyethyl)-chroman, 0.2 g of p-toluenesulfonic acid and 200 ml of toluene was refluxed for 19 hours. The reaction mixture was worked up conventionally to give the above product, which was recrystallized from methanol/water to give colorless crystals of melting point 95°–98° C., in 69% yield.

Using the trans-esterification process, starting from the appropriate methyl propionate, the same compound was obtained in 80% yield.

EXAMPLE 2

6-Hydroxy-2,5,7,8-tetramethyl-2-[2-oxa-3-oxo-6-(3,5-di-tert.-butyl-4-hydroxy)-phenyl]-hex-1-yl-chroman The above compound was obtained as described in Example 1 from 2-hydroxymethylchroman and the phenylpropionic acid derivative mentioned in Example 1. The product, a brownish oil which slowly crystallizes, was obtained in 48% yield.

EXPERIMENTS ON THE STABILIZING ACTION OF THE CHROMAN DERIVATIVES I

1. Color of polypropylene

The color quality was measured in terms of the yellowness index (YI), by the yellowness test (ASTMD 1925).

The test material used was additive-free dechlorinated polypropylene; in each case the stabilizer was incorporated into the polypropylene in the same manner, and the material was then molded into granules of 15 mm layer thickness and sheets of 1 mm thickness. The YI values quoted are each the mean of two measurements. The higher the values, the lower the color quality. The results are shown in the Table. The values roughly correspond to the following (visually) perceptible discolorations of the test material:

2: no discernible discoloration
3–5: very slight discoloration 5–10: slight but distinctly discernible discoloration
10–20: marked discoloration
20: severe discoloration

2. Processing stability of polypropylene

The polypropylene samples (the material used being the same as for the color test) were subjected to six extrusion and granulation sequences. The quotient $MFI_6/MFI_1$ was calculated from the melt indices (MFI) (for method of determination, see DIN 53,735) after the first and sixth extrusions. The higher this quotient, the lower the processing stability. The color measurements correspond to that in the color test. The results are also shown in the Table.

3. Long-term stability of polypropylene

Polypropylene sheets as specified in the color test were subjected to oven aging, as described in DIN 53,383, page 1, by heating the sheets in an oven, with access of fresh air, at 140° C. until they showed noticeable embrittlement. The visual test was carried out every 24 hours, ie. the aging time was measured in days. The lower the values, the lower the long-term stability. The values are mean values of ten measurements, and each has a deviation of up to about 5%. The results are summarized in the Table.

TABLE

| Experiment No. | Stabilizer | from Example No. | Amount % by weight | Color, YI Index after incorporation | Processing stability $MFI_6/MFI_1$ | $\Delta YI$ $(= YI_6 - YI_1)$ | Long-term stability (hours) |
|---|---|---|---|---|---|---|---|
| | comparative | | | | | | |
| 1 | without stabilizer | — | — | 1 | 7.3 | 4 | <24 |
| 2 | $Q^{(x)}$ | — | 0.1 | 8 | 2.5 | 13 | 707 |
| 3 | α-tocopherol | — | 0.1 | 18 | 1.9 | 10 | 70 |
| 4 | α-tocopherol Q | | 0.1 0.5 | 15 | 1.5 | 11 | 215 |
| | according to the invention | | | | | | |
| 5 | ![structure] | 1 | 0.1 | 13 | 1.3 | 18 | 314 |
| 6 | ![structure] | 2 | 0.1 | 12 | 1.2 | 14 | 314 |

$^{(x)}$Neopentyl glycol tetra-[3-(3,5-di-tert.-butyl-4-hydroxyphenyl)-propionate] (a commerical product)

We claim:

1. A chroman derivatives of the general formula I

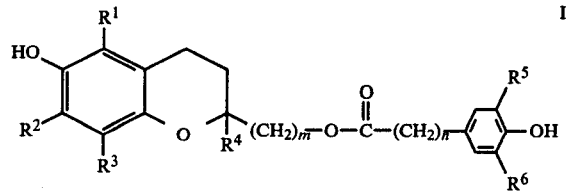

where $R^1$, $R^2$, $R^3$ and $R^4$ are each H or $C_1$–$C_4$-alkyl, $R^5$ is sec.-$C_3$–$C_8$-alkyl or tert.-$C_4$–$C_8$ alkyl, $R^6$ is H or $R^5$, m is 1, 2 or 3, and n is 0, 1, 2 or 3.

* * * * *